United States Patent [19]

Chasar

[11] 4,048,140
[45] Sept. 13, 1977

[54] LIGHT RESISTANT POLYOLEFIN COMPOSITIONS

[75] Inventor: Dwight William Chasar, Northfield, Ohio

[73] Assignee: The B. F. Goodrich Company, Akron, Ohio

[21] Appl. No.: 738,267

[22] Filed: Nov. 2, 1976

[51] Int. Cl.$^2$ .............................................. C08K 5/41
[52] U.S. Cl. ............................................ 260/45.95 C
[58] Field of Search ................ 260/607 AR, 45.95 C; 526/30, 271

[56] References Cited

U.S. PATENT DOCUMENTS

| 2,560,050 | 7/1951 | Cook | 260/607 AR |
| 2,662,061 | 12/1953 | Gilcrease et al. | 260/45.95 C |
| 3,072,601 | 1/1963 | Breslow | 260/607 AR |
| 3,649,695 | 3/1972 | Milionis | 260/45.95 C |

OTHER PUBLICATIONS

Industrial and Engineering Chemistry, vol. 50, May 1958, pp. 797 and 798.

Primary Examiner—V. P. Hoke
Attorney, Agent, or Firm—J. Hughes Powell, Jr.

[57] ABSTRACT

Polyolefins are stabilized against heat and light degradation by including in said polyolefins an unsymmetrical 2-hydroxydiphenyl sulfoxide.

9 Claims, No Drawings

LIGHT RESISTANT POLYOLEFIN COMPOSITIONS

BACKGROUND OF THE INVENTION

Polyolefins are subject in many applications to degradation caused by the deleterious effects of heat and light. Many stabilizers have been employed to protect such polymers from degradation but they have not been completely satisfactory in providing protection from both heat and light degradation, and often introduce color problems. Aromatic sulfur compounds have been used as heat stabilizers for rubber and polyolefins including bis(5-methyl-3-t-butyl-2-hydroxyphenyl) monosulfide. Symmetrical polyhydroxy compounds such as 4,4'-thiobis(resorcinol) and the like have been used in bleaching and stabilizing wood rosin. However, such materials have not been completely satisfactory in providing both heat and light resistance to polymers exposed to heat and light, particularly the polyolefins.

SUMMARY OF THE INVENTION

2-Hydroxydiphenyl sulfoxides (sulfide S-oxide) of the general formula

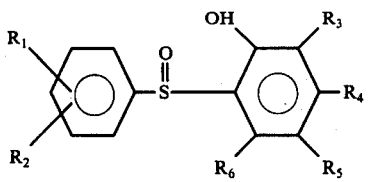

wherein $R_1$ is hydrogen, $R_2$ is a lower alkyl as defined or halogen as defined, wherein $R_3$ is hydrogen or a lower alkyl as defined such as methyl and t-butyl, $R_4$ is hydrogen or lower alkyl as defined such as methyl, $R_5$ is hydrogen or a lower alkyl such as methyl, ethyl, i-propyl, t-butyl, t-pentyl, t-octyl, dodecyl, phenyl, and the like, $R_6$ is hydrogen or lower alkyl as defined as methyl, are useful in protecting polyolefins from the degradative effects of heat and light. Lower alkyl means those radicals containing 1 to 12 carbon atoms, preferably 1 to 8. t-Alkyl groups provide products with an excellent balance of properties. The halogen is chlorine or bromine.

DETAILED DESCRIPTION

The 2-hydroxydiphenyl sulfoxides are prepared by reacting an arylsulfinyl chloride with a phenol.

The arylsulfinyl chlorides are easily prepared by reacting a phenyl mercaptan of the formula

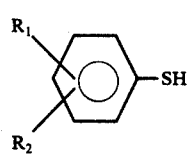

or a diphenyl disulfide of the formula

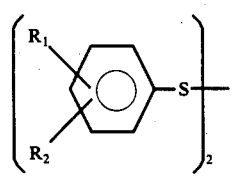

with chlorine and acetic anhydride at $-10°$ C. to form the arylsulfinyl chloride

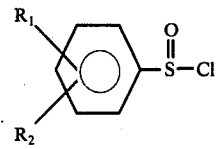

wherein $R_1$, and $R_2$ are normally hydrogen, a halogen such as chlorine, a lower alkyl group containing 1 to 8 carbon atoms including methyl, t-butyl, and the like.

The arylsulfinyl chlorides are reacted with phenols of the general formula

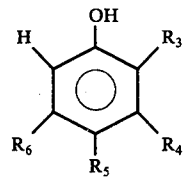

in the presence of aluminum chloride and methylene chloride at 0° C. to provide unsymmetrical 2-hydroxydiphenyl sulfoxides of the general formula

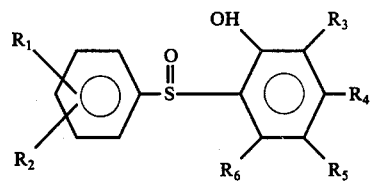

wherein $R_1$ is hydrogen, $R_2$ is a lower alkyl, as defined or halogen as defined, wherein $R_3$ is hydrogen or a lower alkyl as defined such as methyl and t-butyl, $R_4$ is hydrogen or lower alkyl as defined such as methyl, $R_5$ is hydrogen or a lower alkyl as defined such as methyl, ethyl, i-propyl, t-butyl, t-pentyl, t-octyl, dodecyl, phenyl, and the like, $R_6$ is hydrogen or lower alkyl as defined as methyl.

In the reaction of arylsulfinyl chloride with the phenol, about 1 mol of the arylsulfinyl chloride and about one mol of phenol are reacted with at least an equimolar amount of aluminum chloride in a polar solvent at a temperature preferably below about 25° C. If the temperature is conducted at too low a temperature, the reaction is too slow to be practical, and more preferably is greater than about 0° C. While molar excess of reactants may be used, there is no real advantage, and less than molar amounts of a reactant will result in lower yields. A useful solvent is dichloromethane and other solvents including chloroform, benzene, trichloromethane, ethylene dichloride, and the like may be used as solvents. An advantage of this one step reaction is that total yields greater than about 50% can be obtained.

The 2-hydroxydiphenyl sulfoxides in amounts as low as 0.01, more preferably about 0.1 to as high as 5 to 10 weight parts per 100 weight parts of polymer provide increased resistance to heat and light induced degradation in polyolefins.

Polyolefins having molecular weights of at least about 2000 which may be photostabilized in accordance with this invention include homopolymers of α-olefins including those of ethylene, propylene, butene-1, isobutylene, pentene-1, hexene-1, 4-methyl-1-pentene, and the like; copolymers thereof such as ethylene, propylene, ethylene butene-1, 4-methyl-1-pentene, hexene-1, and the like; ethylene α-olefin diene rubbers wherein the α-olefin is preferably propylene or butene-1 and the diene is 1,4-hexadiene, 2-methyl-1,4-hexadiene, dimethyl-1,4,9-decatriene, dicyclopentadiene, vinyl cyclohexane, vinyl norbornene, 2-ethylidene norbornene, norbornadiene, methyl tetrahydroindene, and the like as is well known.

The 2-hydroxydiphenyl sulfoxides are readily incorporated into the polyolefins by conventional methods including powder mixing, milling or banbury mixing, extruding and the like, as such; in a solvent or masterbatched. Conventional compounding ingredients will also be used in conjunction with the sulfoxide; including fillers, reinforcing agents, processing oils, plasticizers, lubricants, curing agents, antioxidants, antiozonants, color and heat stabilizers, other ultraviolet absorbers, and the like.

These sulfoxides have been found to be particularly useful when used in conjunction with other stabilizers, particularly aromatic hydroxy stabilizers, and more particularly, unexpected synergistic activity is obtained with certain hydroxyphenyl alkeneyl isocyanurates of the formula

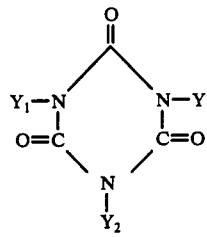

wherein Y is a hydroxyphenylalkyleneyl radical having the formula

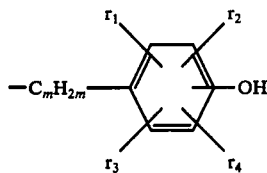

wherein $m$ is an integer from 1 to 4, $r_1$ is an alkyl group positioned immediately adjacent to the hydroxyl group on the ring and contains from 1 to 18 carbon atoms and $r_2$, $r_3$ and $r_4$ are selected from the group consisting of hydrogen or an alkyl group containing from 1 to 18 carbon atoms; and $Y_1$ and $Y_2$ are selected from the group consisting of hydrogen or Y. The amounts of the combination used will be from about 0.5 total to about 10 weight parts per 100 weight parts of polymer in a value of about 1:10 to 10:1 of each.

To demonstrate the practice of the invention, a series of 2-hydroxydiphenyl sulfoxides were prepared and tested for stabilizing activity in polypropylene.

The 2-hydroxydiphenyl sulfoxides used in the practice of this invention are readily prepared by adding one equivalent of the arylsulfinyl chloride dropwise to a well stirred suspension or solution of one equivalent of a substituted phenol and one equivalent of anhydrous aluminum chloride in methylene chloride at 0° C. under a nitrogen atmosphere. This mixture is usually stirred for about 3 hours at this temperature. Water is then slowly added until the solid product in the reaction product is dissolved. The layers are separated and the organic portion is dried over anhydrous magnesium sulfate, filtered and evaporated to a dark oil or solid. The oil or solid reaction product is purified by washing with cold solvent or recrystallized from the solvent. The structure of the 2-hydroxydiphenyl sulfoxides was verified by melting point, infrared or NMR spectroscopy and most by elemental analysis for C, H, and S. The compounds were tested for stabilizing activity by blending the amount shown in the tables as parts per hundred of polypropylene and the blend extruded, pressed into 10 mil thick sheets from which 1 × 2 inch samples were cut. The samples were then molded on cardboard holders of a size to fit an IR spectrometer. The samples were placed in a Xenon weatherometer and at various time intervals the samples were removed and IR spectra from 1910 to 1700 cm$^{-1}$ are recorded. A development of carbonyl groups at 1720 cm$^{-1}$ relative to a reference peak at 1890 cm$^{-1}$ [116] (the carbonyl index) against time is monitored. The time for the carbonyl index to reach about 40 is the failure time. The 2-hydroxydiphenyl sulfoxides were screened for photostabilization activity in polypropylene by mixing into polypropylene 0.1 to 0.5 weight part per 100 weight parts of polypropylene. Samples were tested for heat-antioxidant activity by molded sample plaques separated by porcelain spacers on a glass rod which were placed in a draft oven at 140° C. The failure time is that point in time when any portion of the plaque becomes brittle.

Following the general procedure set forth above, a series of 2-hydroxydiphenyl sulfoxides were prepared using the arylsulfinyl chloride and phenol set forth in the table and the yield, crystallizing solvent and m.p. set forth. The concentration of sulfoxide in weight parts per 100 weight parts of polypropylene are also set forth with the results of the oven and weatherometer aging.

| Aryl sulfinyl chloride | Phenol | Products | % Yield | m.p. (° C) (solvent) | Conc. (phr) | Oven-aging (days) 125° | 140° | 150° | Weatherometer (hours) |
|---|---|---|---|---|---|---|---|---|---|
| Control | — | — | — | — | 0 | 1½ | ½ | ⅛ | 200 |
| Benzenesulfinyl chloride | p-methylphenol | 2-hydroxy-5-methyldiphenyl sulfide S-oxide | 64 | 135-137 (ethyl acetate) | 0.5 | 3½ | 1½ | 1 | 300 |
| Benzenesulfinyl chloride | 2,4-dimethyl phenol | 2-hydroxy-3,5-dimethyldiphenyl sulfide S-oxide | 58 | 97-99 (ethyl acetate) | 0.1 0.5 | 2⅜ 2⅜ | 1 1 | 1 1 | 395 308 |
| Benzenesulfinyl chloride | p-dodecyl phenol | 2-hydroxy-5-dodecyldiphenyl sulfide S-oxide | 96 | oil (crude) | 0.1 | 2⅜ | 1 | 1 | 250 |
| Benzenesulfinyl chloride | 2-t-butyl-4-methyl phenol | 2-hydroxy-3-t-butyl-5-methyldiphenyl sulfide S-oxide | 75 | 66-72 (ethyl acetate) | 0.1 0.5 | 2⅜ 4½ | 1 <4 | 1 1 | 400 292 |
| Benzene- | 4-t-octyl | 2-hydroxy-5-t-octyl- | 20 | 168.5-170.5 | 0.1 | 2⅜ | ⅜ | 1 | 493 |

-continued

| Aryl sulfinyl chloride | Phenol | Products | % Yield | m.p. (° C) (solvent) | Conc. (phr) | Oven-aging (days) 125° | 140° | 150° | Weather-ometer (hours) |
|---|---|---|---|---|---|---|---|---|---|
| sulfinyl chloride | phenol | diphenyl sulfide S-oxide | | (ethyl acetate) | 0.5 | 2⅜ | 1 | 1 | 258 |
| Benzene-sulfinyl chloride | 2-methyl-4-t-butyl phenol | 2-hydroxy-3-methyl-5-t-butyldiphenyl sulfide S-oxide | 69 | 115–116.5 (acetone) | 0.1 | 2⅜ | 1 | 1 | 258 |
| Benzene-sulfinyl chloride | 4-ethyl phenol | 2-hydroxy-5-ethyl-diphenyl sulfide S-oxide | 33 | 141–143 (ethyl acetate) | 0.5 | 3 | 1 | 1 | 258 |
| Benzene-sulfinyl chloride | 4-t-pentyl phenol | 2-hydroxy-5-t-pentyl-diphenyl sulfide S-oxide | 43 | 104–120 (ethyl acetate) | 0.5 | 2⅜ | 1 | 1 | 292 |
| Benzene-sulfinyl chloride | 2,4-di-t-butyl phenol | 2-hydroxy-3,5-di-t-butyldiphenyl sulfide S-oxide | 28 | 90–95 (ethyl alcohol) | 0.5 | 1 | ½ | 1 | |
| Benzene-sulfinyl chloride | 4-t-butyl phenol | 2-hydroxy-5-t-butyl-diphenyl sulfide S-oxide | 23 | 182–184 (ethyl acetate) | 0.1 / 0.5 | 3 / 2⅜ | 1 / 1 | 1 / 1 | 200 / 258 |
| Benzene-sulfinyl chloride | 4-isopropyl phenol | 2-hydroxy-5-iso-propyldiphenyl sulfide S-oxide | 55 | 130–131.5 (ethyl acetate) | 0.1 | 2⅜ | 1 | 1 | 250 |
| Benzene-sulfinyl chloride | 3,5-dimethyl phenol | 2-hydroxy-4,6-dimethyldiphenyl sulfide S-oxide | 50 | oil | 0.1 | 1⅜ | ½ | 1 | |
| p-toluene sulfinyl chloride | 4-methyl phenol | 2-hydroxy-4',5-dimethyldiphenyl sulfide S-oxide | 45 | 180–183 (ethyl alcohol) | 0.1 / 0.5 | 2⅜ / 3½ | 1 / 1 | 1 / 1 | 322 / 292 |
| p-toluene sulfinyl chloride | 4-ethyl phenol | 2-hydroxy-4'-methyl-5-ethyldiphenyl sulfide S-oxide | 68 | 120–122 (ethyl acetate) | 0.1 | 3½ | 1 | 1 | 250 |
| p-toluene sulfinyl chloride | 4-isopropyl phenol | 2-hydroxy-4'-methyl-5-isopropyldiphenyl sulfide S-oxide | 60 | 122.5–124.5 (ethyl acetate) | 0.5 | 2½ | 1 | 1 | 268 |
| p-toluene sulfinyl chloride | 4-t-butyl phenol | 2-hydroxy-4'-methyl-5-t-butyldiphenyl sulfide S-oxide | 69 | 162–165 (acetone) | 0.1 | 2⅜ | 1 | 1 | 258 |
| p-toluene sulfinyl chloride | 4-t-pentyl phenol | 2-hydroxy-4'-methyl-5-t-pentyldiphenyl sulfide S-oxide | 34 | 132–134 (acetone) | 0.1 / 0.5 | 3½ / 3½ | 1 / 1 | 1 / 1 | 493 / 308 |
| p-toluene sulfinyl chloride | 4-t-octyl phenol | 2-hydroxy-4'-methyl-5-t-octyldiphenyl sulfide S-oxide | 47 | 155–157 (acetone) | 0.5 | 2½ | 1 | 1 | 258 |
| p-toluene sulfinyl chloride | 4-phenyl phenol | 2-hydroxy-4'-methyl-5-phenyldiphenyl sulfide S-oxide | 66 | 175–182 (methanol) | 0.5 | 3½ | 1 | 1 | 275 |
| p-toluene sulfinyl chloride | 2,4-dimethyl phenol | 2-hydroxy-3,4',5-trimethyldiphenyl sulfide S-oxide | 56 | 85–87 (ethanol) | 0.1 / 0.5 | 3½ / 3½ | 1 / 1½ | 1 / 1 | 395 / 308 |
| p-toluene sulfinyl chloride | 3,4-dimethyl phenol | 2-hydroxy-4,4',5-trimethyldiphenyl sulfide S-oxide | 54 | 186–189 (ethyl acetate) | 0.5 | 2⅜ | 1 | 1 | 308 |
| p-toluene sulfinyl chloride | 2-methyl-4-t-butyl phenol | 2-hydroxy-3,4'-dimethyl-5-t-butyl-diphenyl sulfide S-oxide | 78 | 127–129 (acetone) | 0.1 | 2⅜ | 1 | 1 | 250 |
| p-toluene sulfinyl chloride | 2-t-butyl-4-methyl phenol | 2-hydroxy-3-t-butyl-4',5-dimethyldiphenyl sulfide S-oxide | 73 | 129–130 (hexane) | 0.1 / 0.5 | 2⅜ / 2½ | 1 / 1 | 1 / 1 | 250 |
| p-toluene sulfinyl chloride | 2,4-di-t-butyl phenol | 2-hydroxy-3,5-di-t-butyl-4'-methyldiphenyl sulfide S-oxide | 66 | 113–115 (methanol) | 0.5 | 2⅜ | 1 | 1 | 308 |
| 4-t-butyl benzene sulfinyl chloride | 4-methyl phenol | 2-hydroxy-4'-t-butyl-5-methyldiphenyl sulfide S-oxide | 32 | 184.5–192 (ethanol) | 0.1 / 0.5 | 1 / 1 | ½ / ½ | 1 / 1 | |

Other compounds prepared include 2-hydroxy-4'-t-butyl-5-phenyldiphenyl sulfide S-oxide and 2-hydroxy-4'-chloro-5-methyldiphenyl sulfide S-oxide.

| Aryl sulfinyl chloride | Phenol | Products | % Yield | m.p. (° C) (solvent) | Conc. (phr) | Oven-aging (days) 125° | 140° | 150° | Weather-ometer (hours) |
|---|---|---|---|---|---|---|---|---|---|
| 4-t-butyl benzene sulfinyl chloride | 2-methyl-4-t-butyl phenol | 2-hydroxy-3-methyl-4',5-di-t-butyl-diphenyl sulfide S-oxide | 78 | 146–148 (methanol) | 0.1 | 1 | ½ | 1 | |
| 4-t-butyl benzene sulfinyl chloride | 2-t-butyl-4-methyl phenol | 2-hydroxy-3,4'-di-t-butyl-5-methyldiphenyl sulfide S-oxide | 90 | oil (crude) | 0.1 | 1 | ½ | 1 | |

I claim:

1. A polyolefin containing a stabilizing amount of a 2-hydroxydiphenyl sulfoxide of the general formula

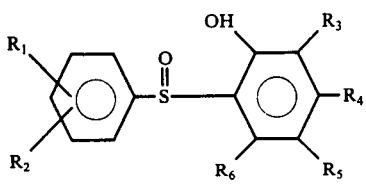

wherein $R_1$ is hydrogen, $R_2$ is a lower alkyl or halogen, $R_3$ is hydrogen or a lower alkyl, $R_4$ is hydrogen or lower alkyl, $R_5$ is hydrogen or a lower alkyl and $R_6$ is hydrogen or lower alkyl.

2. A polyolefin of claim 1 wherein the 2-hydroxydiphenyl sulfoxide is present in amounts of about 0.1 to 10 weight parts per 100 weight parts of polyolefin.

3. A composition of claim 2 wherein said polyolefin is polypropylene.

4. A composition of claim 3 wherein said sulfoxide is 2-hydroxy-4'-methyl-5-t-pentyldiphenyl sulfoxide.

5. A composition of claim 3 wherein said sulfoxide is 2-hydroxy-3,5-dimethyldiphenyl sulfoxide.

6. A composition of claim 3 wherein said sulfoxide is 2-hydroxy-3-t-butyl-5-methyldiphenyl sulfoxide.

7. A composition of claim 3 wherein said sulfoxide is 2-hydroxy-4',5-dimethyldiphenyl sulfoxide.

8. A composition of claim 3 wherein said sulfoxide is 2-hydroxy-5-t-octyldiphenyl sulfoxide.

9. A composition of claim 3 wherein said sulfoxide is 2-hydroxy-3,4',5-trimethyldiphenyl sulfoxide.

* * * * *

UNITED STATES PATENT OFFICE
CERTIFICATE OF CORRECTION

PATENT NO. : 4,048,140
DATED : September 13, 1977
INVENTOR(S) : DWIGHT WILLIAM CHASAR It is certified that error appears in the above-identified patent and that said Letters Patent are hereby corrected as shown below:

Column 2, line 56 delete [trichloromethane] and add --- trichloroethane ---.

Column 4, line 35 delete [$cm^{1161}$] and add in its place --- $cm^{-1}$ --- .

Column 6, under column headed "Weatherometer (Hours)" the eleventh number from the top should read --- 258 --- (not 268).

Signed and Sealed this

Fourth Day of April 1978

[SEAL]

Attest:

RUTH C. MASON
Attesting Officer

LUTRELLE F. PARKER
Acting Commissioner of Patents and Trademarks